(12) United States Patent
Guerrini et al.

(10) Patent No.: US 9,962,447 B2
(45) Date of Patent: May 8, 2018

(54) SUPRAMOLECULAR AGGREGATES COMPRISING MALEIMIDO CORES

(71) Applicant: UFPEPTIDES S.R.L., Bologna (IT)

(72) Inventors: Remo Guerrini, Ferrara (IT); Severo Salvadori, Ferrara (IT); Girolamo Calo', Ferrara (IT)

(73) Assignee: UFPEPTIDES S.R.L., Ferrara (IT)

( * ) Notice: Subject to any disclaimer, the term of this patent is extended or adjusted under 35 U.S.C. 154(b) by 0 days. days.

(21) Appl. No.: 14/782,578

(22) PCT Filed: Apr. 3, 2014

(86) PCT No.: PCT/EP2014/056674
§ 371 (c)(1),
(2) Date: Oct. 5, 2015

(87) PCT Pub. No.: WO2014/161926
PCT Pub. Date: Oct. 9, 2014

(65) Prior Publication Data
US 2016/0051689 A1  Feb. 25, 2016

(30) Foreign Application Priority Data

Apr. 5, 2013  (EP) .................................... 13162532

(51) Int. Cl.
| | | |
|---|---|---|
| *C07D 403/14* | (2006.01) | |
| *A61K 47/48* | (2006.01) | |
| *A61K 38/17* | (2006.01) | |
| *A61K 47/54* | (2017.01) | |
| *A61K 47/55* | (2017.01) | |

(52) U.S. Cl.
CPC .... *A61K 47/48061* (2013.01); *A61K 38/1787* (2013.01); *A61K 47/543* (2017.08); *A61K 47/545* (2017.08); *A61K 47/55* (2017.08); *C07D 403/14* (2013.01)

(58) Field of Classification Search
None
See application file for complete search history.

(56) References Cited

FOREIGN PATENT DOCUMENTS

WO   2007/144685 A1   12/2007

OTHER PUBLICATIONS

Röhrich et al., "A Novel Tetrabranched Neurotensin(8-13) Cyclam Derivative: Synthesis, 64Cu-labeling and Biological Evaluation," Journal of Inorganic Biochemistry 105(6):821-832 (2011).
Zhang et al., "Macrocyclic Chelator Assembled RGD Multimers for Tumor Targeting," Bioorganic & Medicinal Chemistry Letters 21(11):3423-3426 (2011).
Kraus et al., "Cyclic Tetrameric Clusters of Chemotactic Peptides as Superactive Activeators of Lysozyme Release From Human Neutrophils," Biochemical and Biophysical Research Communications 124(3):939-944 (1984).
Li et al, "Synthesis and Anti-HIV Activity of Trivalent CD4-mimetic Miniproteins," Bioorganic & Medicinal Chemistry 15(12):4220-4228 (2007).
Shunzi et al., "Synthesis and Characterization of a High-affinity Alpha v Beta 6-specific Ligand for In Vitro and In Vivo Applications," Molecular Cancer Therapeutics 8(5):1239-1249 (2009).
Bracci et al., "Synthetic Peptides in the Form of Dendrimers Become Resistant to Protease Activity," Journal of Biological Chemistry 278(47):46590-46595 (2003).
Guerrini et al., "A Novel and Facile Synthesis of Tetra Branched Derivatives of Nociceptin/Orphanin FQ," Bioorganic & Medicinal Chemistry 22(14):3703-3712 (2014).
International Search Report and Written Opinion for corresponding PCT/EP2014/056674, filed Apr. 3, 2014 (dated Aug. 7, 2014.

*Primary Examiner* — Noble E Jarrell
(74) *Attorney, Agent, or Firm* — LeClairRyan PLLC

(57) ABSTRACT

The invention relates to a supramolecular aggregate of formula (VI) wherein A is an active substance, and $X_1$, $X_2$, $X_3$ and $X_4$, independently to each other, are a moiety of Formula (I) containing a maleimido functionalization and at least one among $X_1$, $X_2$, $X_3$ and $X_4$ is present in Formula (VI). In a preferred embodiment the maleimido-functionalized core is PWT2. The supra-molecular aggregate can be used in the field of drugs, vaccines, as ligands for GPCR, i.e. agonists as well as antagonist, as antibiotics and as diagnostics eventually in complex with radionuclides.

8 Claims, 10 Drawing Sheets

PWT2-N/OFQ

N/OFQ = Phe$^1$-Gly-Gly-Phe-Thr-Gly-Ala-Arg$^8$-Lys-Ser-Ala-Arg-Lys-Leu-Ala-Asn-Gln$^{17}$

SEQUENCE LISTING

```
<160> NUMBER OF SEQ ID NOS: 26

<210> SEQ ID NO 1
<211> LENGTH: 13
<212> TYPE: PRT
<213> ORGANISM: Artificial Sequence
<220> FEATURE:
<223> OTHER INFORMATION: Afamelanotide a synthetic analog of the
      naturally-occurring melanocortin peptide hormone alpha-melanocyte
      stimulating hormone (a-MSH)
<220> FEATURE:
<221> NAME/KEY: MOD_RES
<222> LOCATION: (4)..(4)
<223> OTHER INFORMATION: Norleucine

<400> SEQUENCE: 1

Ser Tyr Ser Xaa Glu His Phe Arg Trp Gly Lys Pro Val
1               5                   10

<210> SEQ ID NO 2
<211> LENGTH: 28
```

```
<212> TYPE: PRT
<213> ORGANISM: Artificial Sequence
<220> FEATURE:
<223> OTHER INFORMATION: Aviptadil

<400> SEQUENCE: 2

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 3
<211> LENGTH: 20
<212> TYPE: PRT
<213> ORGANISM: Artificial Sequence
<220> FEATURE:
<223> OTHER INFORMATION: Bivalirudin

<400> SEQUENCE: 3

Phe Pro Arg Pro Gly Gly Gly Gly Asn Gly Asp Phe Glu Glu Ile Pro
1               5                   10                  15

Glu Glu Tyr Leu
            20

<210> SEQ ID NO 4
<211> LENGTH: 14
<212> TYPE: PRT
<213> ORGANISM: Artificial Sequence
<220> FEATURE:
<223> OTHER INFORMATION: Bombesin
<220> FEATURE:
<221> NAME/KEY: MOD_RES
<222> LOCATION: (1)..(1)
<223> OTHER INFORMATION: Pyroglutamic acid

<400> SEQUENCE: 4

Xaa Gln Arg Leu Gly Asn Gln Trp Ala Val Gly His Leu Met
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Bradykinin

<400> SEQUENCE: 5

Arg Pro Pro Gly Phe Ser Pro Phe Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Cetrorelix
<220> FEATURE:
<221> NAME/KEY: MOD_RES
<222> LOCATION: (1)..(1)
<223> OTHER INFORMATION: (Acetyl-D-3-(2'-naphtyl)-alanine-D-4-
      chlorophenylalanine-D-3-(3'-pyridyl)-alanine
<220> FEATURE:
<221> NAME/KEY: MOD_RES
<222> LOCATION: (4)..(4)
<223> OTHER INFORMATION: D-citrulline

<400> SEQUENCE: 6

Xaa Ser Tyr Xaa Leu Arg Pro Ala
```

```
<210> SEQ ID NO 7
<211> LENGTH: 9
<212> TYPE: PRT
<213> ORGANISM: Artificial Sequence
<220> FEATURE:
<223> OTHER INFORMATION: Buserelin
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (6)..(6)
<223> OTHER INFORMATION: Ser(OtBu)

<400> SEQUENCE: 7

Xaa His Trp Ser Tyr Xaa Leu Arg Pro
1               5

<210> SEQ ID NO 8
<211> LENGTH: 11
<212> TYPE: PRT
<213> ORGANISM: Artificial Sequence
<220> FEATURE:
<223> OTHER INFORMATION: Eledoisin
<220> FEATURE:
<221> NAME/KEY: MOD_RES
<222> LOCATION: (1)..(1)
<223> OTHER INFORMATION: Pyroglutamic acid

<400> SEQUENCE: 8

Xaa Pro Ser Lys Asp Ala Phe Ile Gly Leu Met
1               5                   10

<210> SEQ ID NO 9
<211> LENGTH: 36
<212> TYPE: PRT
<213> ORGANISM: Artificial Sequence
<220> FEATURE:
<223> OTHER INFORMATION: Enfuvirtide

<400> SEQUENCE: 9

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 10
<211> LENGTH: 39
<212> TYPE: PRT
<213> ORGANISM: Artificial Sequence
<220> FEATURE:
<223> OTHER INFORMATION: Exenatide

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 11
<211> LENGTH: 28
<212> TYPE: PRT
<213> ORGANISM: Artificial Sequence
<220> FEATURE:
<223> OTHER INFORMATION: Ghrelin
<220> FEATURE:
<221> NAME/KEY: MOD_RES
<222> LOCATION: (3)..(3)
<223> OTHER INFORMATION: Ser(Octanoyl)

<400> SEQUENCE: 11

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 12
<211> LENGTH: 6
<212> TYPE: PRT
<213> ORGANISM: Artificial Sequence
<220> FEATURE:
<223> OTHER INFORMATION: GHRP-6

<400> SEQUENCE: 12

His Trp Ala Trp Phe Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: GHRP-2
<220> FEATURE:
<221> NAME/KEY: MOD_RES
<222> LOCATION: (2)..(2)
<223> OTHER INFORMATION: Beta-Naphthalenyl

<400> SEQUENCE: 13

Ala Xaa Ala Trp Phe Lys
 1               5

<210> SEQ ID NO 14
<211> LENGTH: 6
<212> TYPE: PRT
<213> ORGANISM: Artificial Sequence
<220> FEATURE:
<223> OTHER INFORMATION: Hexarelin

<400> SEQUENCE: 14

His Trp Ala Trp Phe Lys
 1               5

<210> SEQ ID NO 15
<211> LENGTH: 10
<212> TYPE: PRT
<213> ORGANISM: Artificial Sequence
<220> FEATURE:
<223> OTHER INFORMATION: Icatibant
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (6)..(6)
<223> OTHER INFORMATION: B-(2-Thienyl)-alanine
<220> FEATURE:
<221> NAME/KEY: MOD_RES
```

```
<222> LOCATION: (8)..(8)
<223> OTHER INFORMATION: Tetrahydro-isoquinoline-3-carboxylic acid
<220> FEATURE:
<221> NAME/KEY: MOD_RES
<222> LOCATION: (9)..(9)
<223> OTHER INFORMATION: Octahydroindole-2-carboxylic acid

<400> SEQUENCE: 15

Arg Arg Pro Xaa Gly Xaa Ser Xaa Xaa Arg
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Neuropeptide S

<400> SEQUENCE: 16

Ser Phe Arg Asn Gly Val Gly Thr Gly Met Lys Lys Thr Ser Phe Gln
1               5                   10                  15

Arg Ala Lys Ser
            20

<210> SEQ ID NO 17
<211> LENGTH: 6
<212> TYPE: PRT
<213> ORGANISM: Artificial Sequence
<220> FEATURE:
<223> OTHER INFORMATION: Opiod peptides

<400> SEQUENCE: 17

Lys Ala Lys Glu Gly Val
1               5

<210> SEQ ID NO 18
<211> LENGTH: 6
<212> TYPE: PRT
<213> ORGANISM: Artificial Sequence
<220> FEATURE:
<223> OTHER INFORMATION: Opioid peptides

<400> SEQUENCE: 18

Lys Thr Lys Gln Gly Val
1               5

<210> SEQ ID NO 19
<211> LENGTH: 6
<212> TYPE: PRT
<213> ORGANISM: Artificial Sequence
<220> FEATURE:
<223> OTHER INFORMATION: Opioid peptides

<400> SEQUENCE: 19

Lys Thr Lys Glu Gly Val
1               5

<210> SEQ ID NO 20
<211> LENGTH: 6
<212> TYPE: PRT
<213> ORGANISM: Artificial Sequence
<220> FEATURE:
<223> OTHER INFORMATION: Opioid peptides

<400> SEQUENCE: 20

Lys Thr Lys Glu Gln Val
1               5
```

```
<210> SEQ ID NO 21
<211> LENGTH: 6
<212> TYPE: PRT
<213> ORGANISM: Artificial Sequence
<220> FEATURE:
<223> OTHER INFORMATION: Opioid peptides

<400> SEQUENCE: 21

Lys Thr Val Glu Gly Ala
1               5

<210> SEQ ID NO 22
<211> LENGTH: 24
<212> TYPE: PRT
<213> ORGANISM: Artificial Sequence
<220> FEATURE:
<223> OTHER INFORMATION: Tetracosactide

<400> SEQUENCE: 22

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 23
<211> LENGTH: 5
<212> TYPE: PRT
<213> ORGANISM: Artificial Sequence
<220> FEATURE:
<223> OTHER INFORMATION: Thymopentin

<400> SEQUENCE: 23

Arg Lys Asp Val Tyr
1               5

<210> SEQ ID NO 24
<211> LENGTH: 28
<212> TYPE: PRT
<213> ORGANISM: Artificial Sequence
<220> FEATURE:
<223> OTHER INFORMATION: Thymosin a-1

<400> SEQUENCE: 24

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 25
<211> LENGTH: 9
<212> TYPE: PRT
<213> ORGANISM: Artificial Sequence
<220> FEATURE:
<223> OTHER INFORMATION: Vx-001

<400> SEQUENCE: 25

Tyr Leu Phe Phe Tyr Arg Lys Ser Val
1               5

<210> SEQ ID NO 26
<211> LENGTH: 4
```

```
<212> TYPE: PRT
<213> ORGANISM: Artificial Sequence
<220> FEATURE:
<223> OTHER INFORMATION: Tuftsin

<400> SEQUENCE: 26

Thr Lys Pro Arg
1
```

SUPRAMOLECULAR AGGREGATES COMPRISING MALEIMIDO CORES

This application is a national stage application under 35 U.S.C. § 371 of PCT Application No. PCT/EP2014/056674, filed Apr. 3, 2014, which claims the priority benefit of European Application No. 13162532.9, filed Apr. 5, 2013, both of which are hereby incorporated by reference in their entirety.

FIELD OF THE INVENTION

This invention relates to supramolecular aggregates of general formula (VI) and their employment for targeting and optionally delivering active substances. In particular, the invention relates to new maleimido-functionalized cores forming the supramolecular aggregates with active substances.

STATE OF THE ART

Chemical strategies for the design of multimeric macrolecules have been described in the recent literature (B. D. Mather et al. Prog. Polym. Sci. 31 (2006) 487-531; K. Sadler et al. Reviews in Molecular Biotechnology 90, (2002) 195-229. The first example of such molecules of peptide nature was proposed by Tam and co-workers (K. J. Chang et al. Proc. Natl. Acad. Sci. USA 85, (1988) 4929-4933) as a solution to increase peptide size while maintaining the original amino acid sequence. Molecules designed by Tam were employed as "octopus immunogen" for generating antibody and this kind of immunization strategy has been named multiple antigen peptide (MAP) strategy. The observation of MAP resistance to proteolysis opened new perspectives for the use of peptides as drugs. To this regard, MAP strategy was applied for the synthesis of branched peptide as cobra-toxin antidotes, as antimicrobial agents, as carrier for tumor targeting etc (A. Pini et al. Current Protein and Peptide Science 9, (2008) 468-477). In addition, a small set of neuropeptides, including enkephalins, neurotensin and nociceptin/orphanin FQ (N/OFQ), were synthesized in monomeric and tetrabranched forms and incubated with human plasma and serum. All the tetrabranched neuropeptides retained full biological activity and generally showed higher stability to blood and brain protease activity (L. Bracci et al. J. Biol. Chem. 278, (2003) 56590-56595). Collectively, these data supported the development of branched peptide molecules as innovative therapeutics. Furthermore, the bigger are the final multimeric macromolecoles as supramolecular aggregates the more complex is their synthesis, purification and analytical characterization. In fact, the impurities generated during MAP assembly by standard solid phase synthesis techniques can not be removed during purification steps especially when long arms are needed. HPLC profile reported in FIG. 4 panel C of the paper (A. Pini et al. Current Protein and Peptide Science 9, (2008) 468-477) displays the low purity grade of the tetrabranched MAP investigated. The low purity grade of MAP molecules obtained by standard solid phase peptide synthesis techniques represents an important issue that need to be solved for the development of branched molecules, i.e. supramolecular aggregates as drugs.

In Zhang Xiaofen et al "Macrocyclic chelator assembled RGD multimers for tumor targeting", Bioorganics & Medicinal Chemistry Letters, Vol. 21, no. 11, June 2011, a macrocyclic chelator, 1,4,7,10-tetrazacyclododecane-1,4,7,10-tetracetic acid (DOTA) for the assembly of peptides in targeting tumour is described. Due to the structure of DOTA the yields of the final multimeric functionalized product decreased as soon as the DOTA was more functionalized, so that the yield of DOTA with 4 peptides was very low.

Therefore it is very difficult to prepare new supramolecular aggregates capable to guarantee not only high yields when prepared even completed functionalized, but also to maintain the link to the molecules to be targeted to the final site with high purity. On the other hand, the supramolecular aggregates should guarantee also the link to the final target in a reproducible way.

The object of the present invention is therefore to provide supramolecular aggregate without using long and difficult purification steps, with high yield. Furthermore, there is a need to provide new supramolecular aggregates, which are capable to link and target active substances in a stable and reproducible way.

SUMMARY OF THE INVENTION

The aforestated objects have hence been attained by means of a supramolecular aggregate of formula (VI)

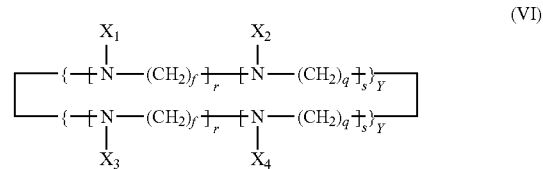

wherein f, q are independently each other an integer from 1 to 8, r and s are independently each other an integer from 1 to 4, Y is an integer from 1 to 4, and $X_1$, $X_2$, $X_3$ and $X_4$, independently to each other, are a moiety of Formula (I) and

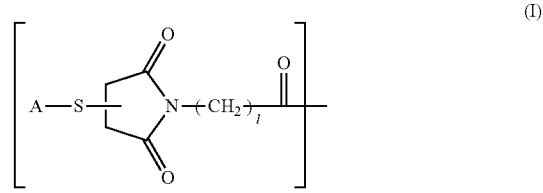

at least one among $X_1$, $X_2$, $X_3$ and $X_4$ is present and wherein

A—S— is an active substance derived with a thiol group or an active substance having a free thiol group and I is an integer from 1 to 10.

In the present invention when the definition "active substance" for A-S—is used, it is intended an active substance, such as a drug, a vaccine, a diagnostic substance to be targeted and delivered to the target site.

The aggregate of Formula (VI) is composed of a core of Formula (IV)

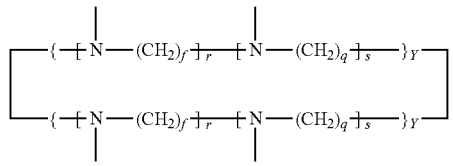

(IV)

and $X_1$ and/or $X_2$, $X_3$ and $X_4$.

In another aspect, the present invention relates to a maleimido functionalized core of formula PWT2

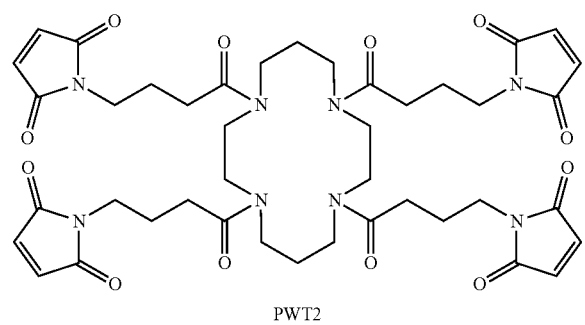

PWT2

The present invention therefore solves the above mentioned problem (i.e. low purity of branched molecules) by providing novel branched scaffolds as supramolecular aggregates containing a maleimido moiety. Such maleimido moieties linked to the branched core allow high yield thiol-michael addition reaction and hence can be used for the chemoselective welding of molecules containing a thiol group. In view of the high yield and chemoselectivity of the reaction employed, the resulting supramolecular aggregates can be easily purified. In addition, the mild conditions required for and the quickness of the welding reaction between maleimido containing cores and thio-derived active substances extend advantageously the use of such approach to active substances with low chemical stability.

In another aspect therefore the invention relates to a process for preparing the supramolecular aggregate of the invention comprising the step of reacting in a thiol-Michael addition n(A-SH) a compound of Formula (VII)

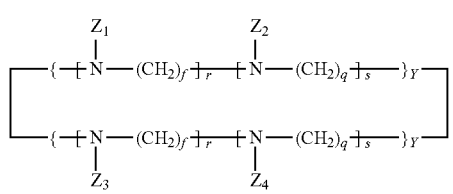

(VII)

wherein f, q are independently each other an integer from 1 to 8, r and s are independently each other an integer from 1 to 4, Y is an integer from 1 to 4, and $Z_1$, $Z_2$, $Z_3$ and $Z_4$, independently each other, are a moiety of Formula (II)

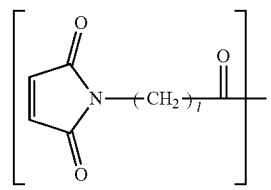

(II)

and at least one among $Z_1$, $Z_2$, $Z_3$ and $Z_4$ is present and I is an integer from 1 to 10.

In the present invention therefore the compound of Formula (VII) is preferably PWT2.

The new maleimido-functionalized cores of Formula (IV), I.e. compounds of Formula (VII), more particularly PWT2, resulted structurally capable to provide for not only a precise link at the thiol group with a specific active substance, but also to target such an active substance in a reproducible way to a targeted site.

Without being bound to any theory the inventors deem that the surprising property of a precise, reproducible and stable link to an active substance and the efficacious targeting to a target site is due to the specific structure of maleimido-functionalized cores of (IV), more preferably as PWT2.

In another aspect the invention relates to a supramolecular aggregate for use in targeting, and optionally delivering, an active substance A to the target site.

The resulting supramolecular aggregates can be used for example, in the field of drugs, vaccines, as ligands for GPCR (agonists as well as antagonists), as antibiotics, as diagnostics (i.e. for PWT2 derivatives as radioligands) and in all the fields were the welding of a single bioactive pharmacophoric unit onto a multifunctional scaffold may be valuable.

DESCRIPTION OF THE FIGURES

The invention is described in detail hereinafter with reference to the accompanying figures in which.

DETAILED DESCRIPTION OF THE INVENTION

Figure 1:
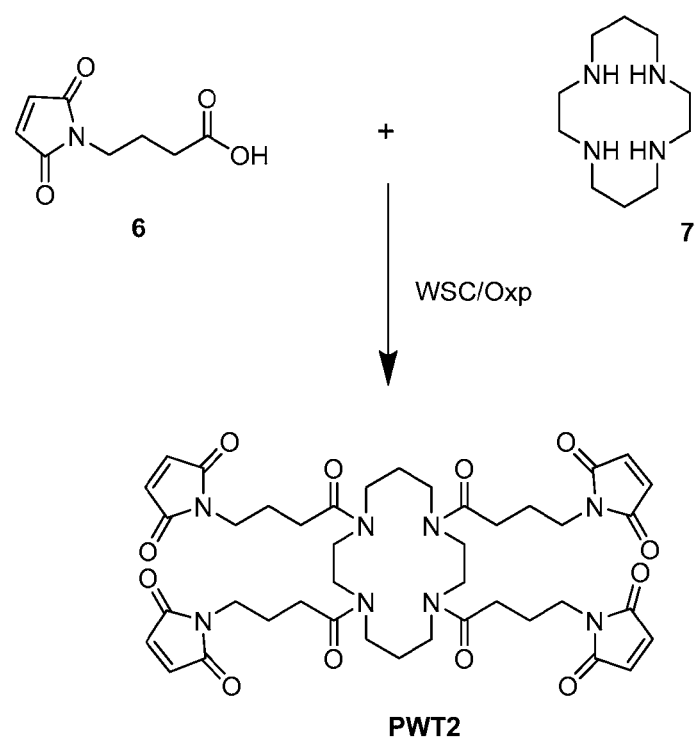
FIG. 1 shows the synthesis scheme of PWT2
Figure 2:
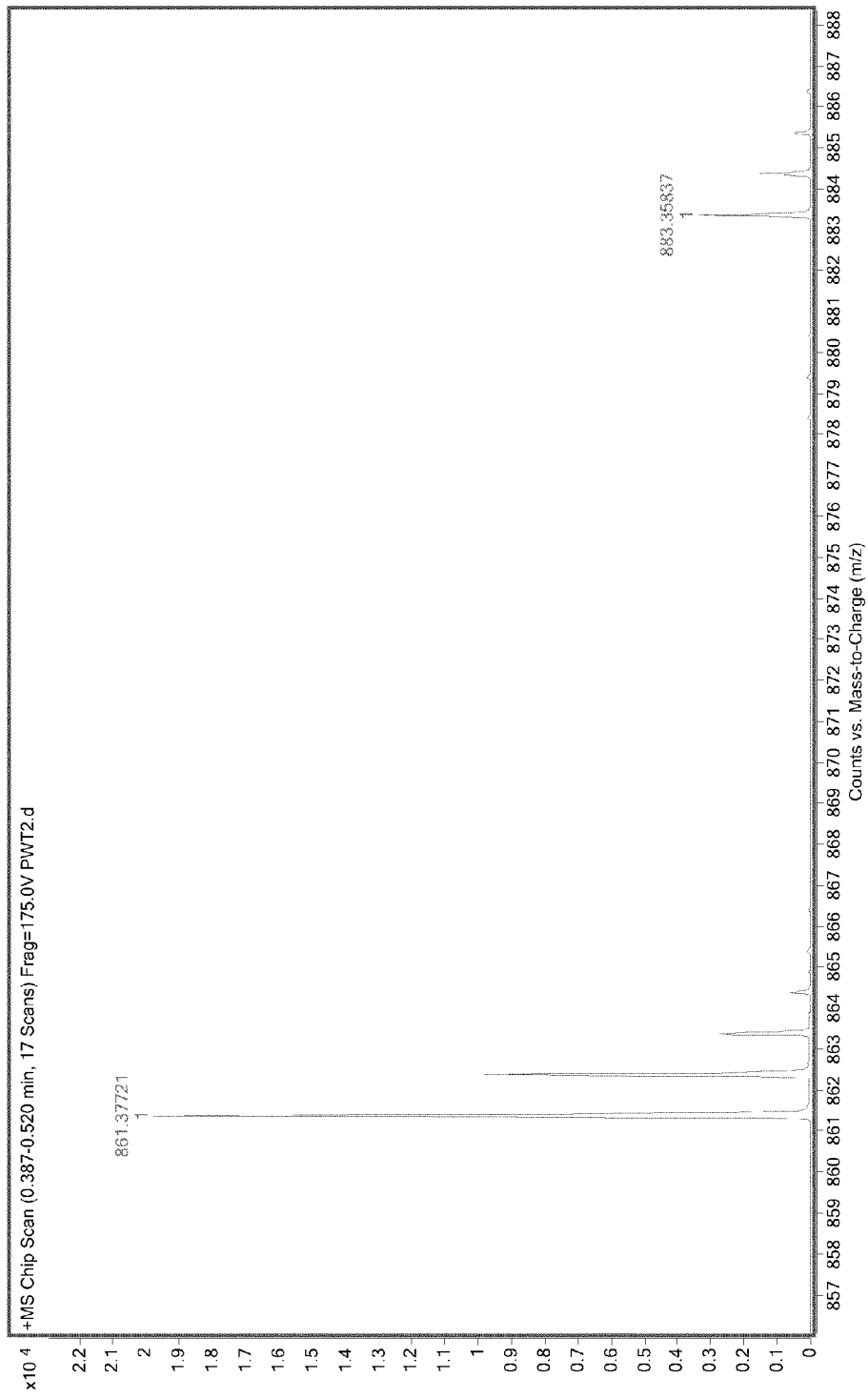
FIG. 2 shows the mass spectrum of PWT2 (calculated M.W. 861.37775) (calculated PWT2+Na MW 883.35969)
Figure 3:
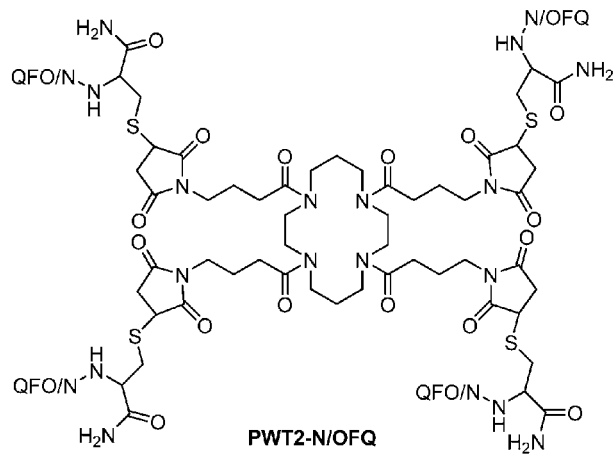
FIG. 3 shows the chemical formula and HPLC profile of PWT2-N/OFQ
Figure 3:
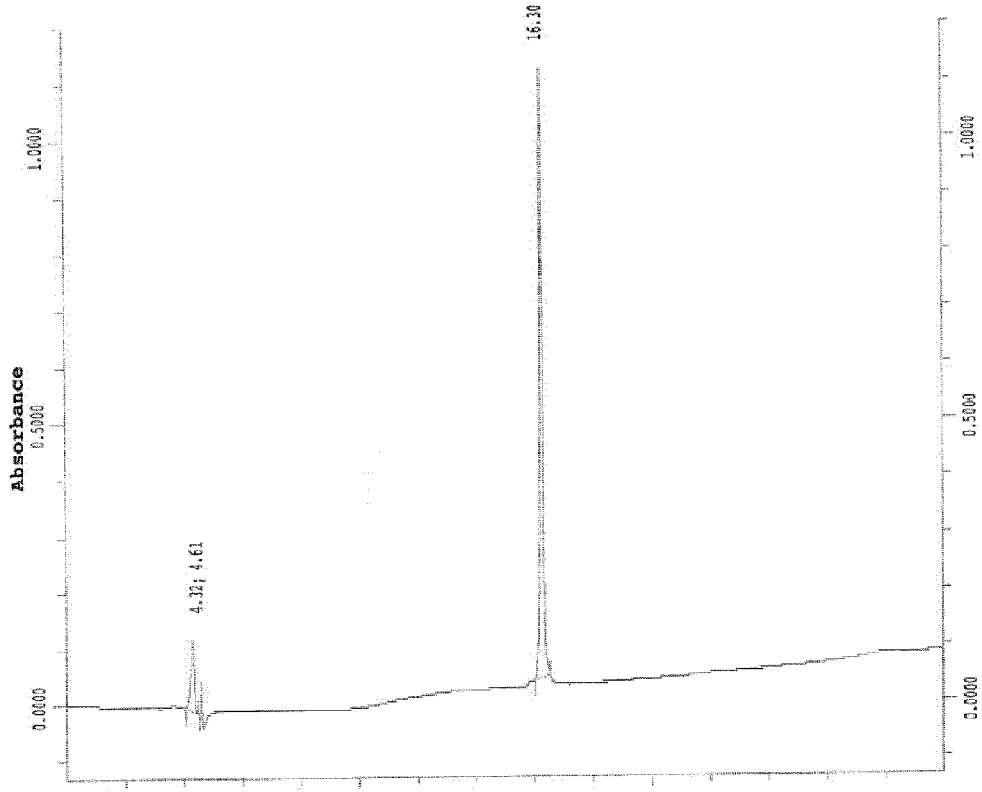
Figure 4:
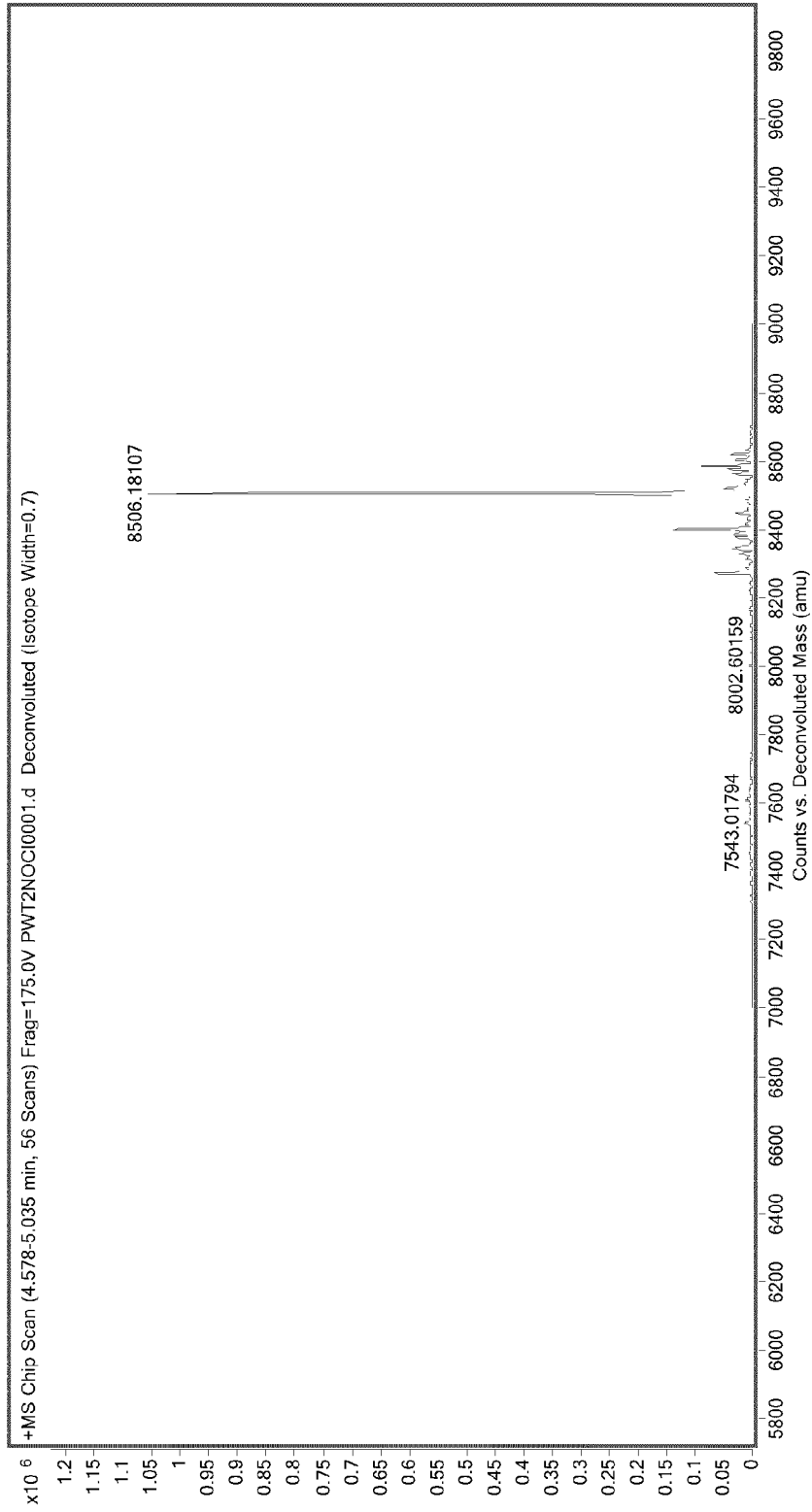
FIG. 4 shows the mass spectrum of PWT2-N/OFQ (calculated M.W. 8505.69)

The invention therefore relates a supramolecular aggregate of formula (VI)

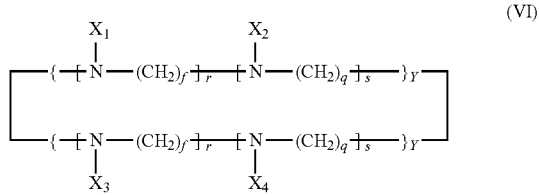

(VI)

wherein f, q are independently each other an integer from 1 to 8, r and s are independently each other an integer from 1 to 4, Y is an integer from 1 to 4, and $X_1$, $X_2$, $X_3$ and $X_4$, independently to each other, are a moiety of Formula (I) and

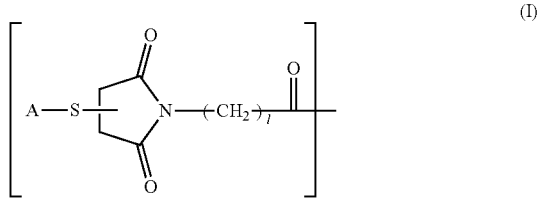

(I)

at least one among $X_1$, $X_2$, $X_3$ and $X_4$ is present and wherein

A-S— is an active substance derived with a thiol group or an active substance having a free thiol group and I is an integer from 1 to 10.

In the present invention when the definition "active substance" for A-S— is used, it is intended an active substance, such as a drug, a vaccine, a diagnostic substance to be targeted and delivered to the target site.

The aggregate of Formula (VI) is composed of a core of Formula (IV)

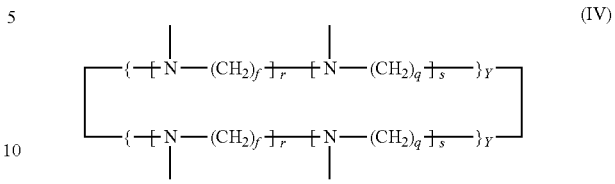

(IV)

and at least one moiety among $X_1$ and/or $X_2$, $X_3$ and $X_4$.

In the aggregate of Formula (VI) and in the core of Formula (IV) f, q are independently each other an integer from 1 to 8, preferably f is 3 and q is 2, r and are independently each other an integer from 1 to 4, preferably they are equal to 1, and Y is an integer from 1 to 4, more preferably is 1. In the moiety of Formula (I) of the supramolecular aggregate of the invention I is 3.

According to the invention in the supramolecular aggregate (VI) $X_1$, $X_2$, $X_3$ and $X_4$ are, independently to each other, linked maleimido fragments which are in turn linked through a thiol group to the active substance A, derived with a thiol group or having the thiol group.

The present invention relates hence to a maleimido-functionalized core of formula (IV).

In another aspect, the present invention relates to a maleimido-functionalized core of formula PWT2

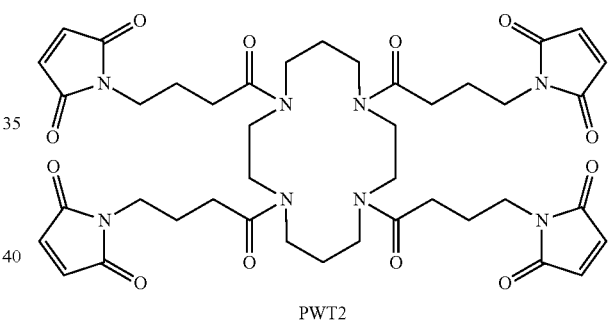

PWT2

The maleimido-functionalized core is linked to a thiol-active substance A.

In another aspect therefore the invention relates to a process for preparing the supramolecular aggregate of the invention comprising the step of reacting in a thiol-Michael addition n(A-SH) a compound of Formula (VII)

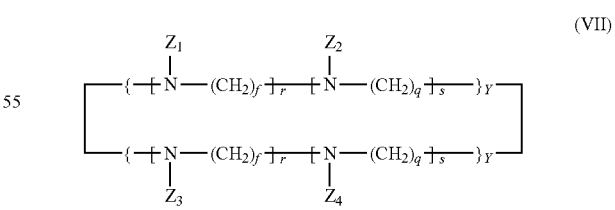

(VII)

wherein f, q are independently each other an integer from 1 to 8, r and s are independently each other an integer from 1 to 4, Y is an integer from 1 to 4, and $Z_1$, $Z_2$, $Z_3$ and $Z_4$, independently each other, are a moiety of Formula (II)

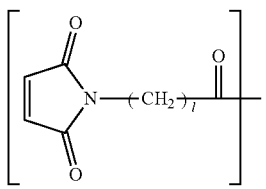

(II)

and at least one among $Z_1$, $Z_2$, $Z_3$ and $Z_4$ is present and I is an integer from 1 to 10.

In a more preferred embodiment the compound of Formula (VII) is PWT2.

The active substance A is preferably selected from the group consisting of

Afamelanotide
Ac-Ser-Tyr-Ser-Nle-Glu-His-D-Phe-Arg-Trp-Gly-Lys-Pro-Val-NH$_2$ (SEQ ID NO:1)
(a synthetic analog of the naturally-occurring melanocortin peptide hormone alpha-melanocyte stimulating hormone (α-MSH))

Aviptadil
His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ (SEQ ID NO:2)

Bivalirudin
D-Phe-Pro-Arg-Pro-Gly-Gly-Gly-Gly-Asn-Gly-Asp-Phe-Glu-Glu-Ile-Pro-Glu-Glu-Tyr-Leu-OH (SEQ ID NO:3)
Hirudin and related direct thrombin inhibitor peptides Bombesin
Pyr-Gln-Arg-Leu-Gly-Asn-Gln-Trp-Ala-Val-Gly-His-Leu-Met-NH2 (SEQ ID NO:4)
(Pyr; pyroglutamic acid) and related analogues.

Bradykinin
Arg-Pro-Pro-Gly-Phe-Ser-Pro-Phe-Arg-OH (SEQ ID NO:5), and related analogues Cetrorelix
Ac-D-Nal-D-Cpa-D-Pal-Ser-Tyr-D-Cit-Leu-Arg-Pro-D-Ala-NH2 (SEQ ID NO:6)
(Acetyl-D-3-(2'-naphtyl)-alanine-D-4-chlorophenylalanine-D-3-(3'-pyridyl)-alanine-L-serine-L-tyrosine-D-citrulline-L-leucine-L-arginine-L-proline-D-alanine-amide)
and related gonadotropin-releasing hormone antagonist such as Abarelix, Degarelix, Ganirelix.

Buserelin
Pyr-His-Trp-Ser-Tyr-D-Ser(OtBu)-Leu-Arg-Pro-NHEt (SEQ ID NO:7)
(Pyr; pyroglutamic acid) and related gonadotropin-releasing hormone agonist such as: Gonodorelin, Boserelin, Deslorelin, Histrelin, Leuprolide, Nafarelin, Triptorelin Goserelin.

Carnosine
Beta-Ala-His-OH

Eledoisin
Pyr-Pro-Ser-Lys-Asp-Ala-Phe-Ile-Gly-Leu-Met-NH2 (SEQ ID NO:8) (Pyr; pyroglutamic acid)

Enfuvirtide
Ac-Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Ala-Ser-Leu-Trp-Asn-Trp-Phe-NH$_2$ (SEQ ID NO:9)

Exenatide
His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO:10)

and related glucagon-like-peptide-1 (GLP-1) receptor agonists such as: Liraglutide Ghrelin
Gly-Ser-Ser(Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-OH (SEQ ID NO:11)
and related growth hormone secretagogue receptor agonists such as: Sermorelin, Tesamorelin GHRP-6
His-D-Trp-Ala-Trp-D-Phe-Lys-NH$_2$ (SEQ ID NO:12)
and related Growth hormone releasing peptide (GHRP) such as GHRP-2 (D-Ala-D-β-Nal-Ala-Trp-D-Phe-Lys-NH2) (SEQ ID NO:13) Hexarelin (His-2-Me-D-Trp-Ala-Trp-D-Phe-Lys-NH$_2$) (SEQ ID NO:14)

Icatibant
D-Arg-Arg-Pro-Hyp-Gly-Thi-Ser-Tic-Oic-Arg-OH (SEQ ID NO:15)
and related bradikinin receptor (B2) antagonists Neuropeptide S
Ser-Phe-Arg-Asn-Gly-Val-Gly-Thr-Gly-Met-Lys-Lys-Thr-Ser-Phe-Gln-Arg-Ala-Lys-Ser-OH (SEQ ID NO:16)
and related analogues Opioid peptides, including enkephalin, dermorphin, deltorphin, dynorphin, endomorphin, nociceptin/orphanin FQ and related analogues Peptide sequences such as:
Lys-Ala-Lys-Glu-Gly-Val (SEQ ID NO:17)
Lys-Thr-Lys-Gln-Gly-Val (SEQ ID NO:18)
Lys-Thr-Lys-Glu-Gly-Val (SEQ ID NO:19)
Lys-Thr-Lys-Glu-Gln-Val (SEQ ID NO:20)
Lys-Thr-Val-Glu-Gly-Ala (SEQ ID NO:21)
Hexadecapeptide with all L and all D Ac-(Lys-Phe)$_8$ Tetracosactide
Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-OH (SEQ ID NO:22)

Synthetic ACTH analogues
Thymopentin
Arg-Lys-Asp-Val-Tyr-OH (SEQ ID NO:23)
Thymosin α-1
Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH (SEQ ID NO:24)

Vx-001
Tyr-Leu-Phe-Phe-Tyr-Arg-Lys-Ser-Val-OH (SEQ ID NO:25)

Tuftsin
Thr-Lys-Pro-Arg (SEQ ID NO:26)

ACE inhibitors, including pseudo-peptides and peptidomimetics as alacepril, benazepril, captopril, cilazapril, delapril, enalapril, fosinopril, imidapril, lisinopril, moexipril, perindopril, quinapril, ramipril, spirapril, temocapril, trandolapril, zofenopril.

H1 antagonists, including ketotifen, azatadine, cetrizine, loratadine

Beta2 adrenergic-agonists, including salbutamol, salmeterol, clenbuterol.

Preferred active substances A are opioid peptides or neuropeptide S (NPS) correlated analogues NPS, more preferably said active substance is selected from the group consisting of enkephalin, dermorphin, deltorphin, dynorphin, endomorphin, nociceptin/orphanin FQ and NPS, still more preferably it is nociceptin/orphanin FQ or NPS.

Supramolecular aggregates are prepared by linking a $Z_1$, $Z_2$, $Z_3$, $Z_4$-functionalized core of formula (VII) with a thiol-derived substance through the thiol-Michael addition reaction, preferably in the presence of an activating mixture.

The maleimido functionalized cores can be prepared both in solution and in solid phase organic chemistry synthesis, or any combination thereof. The maleimido functionalized core (for example PWT2) are then reacted with an active substance containing or derived with a thiol group to give the supramolecular aggregates of the invention.

The new maleimido-functionalized core of Formula (IV) (as compound of Formula (VII)) resulted structurally capable to provide for not only a precise link at the thiol group with a specific active substance, but also to target such an active substance in a reproducible way to a target site. Without being bound to any theory the inventors deem that the surprising property of a precise, reproducible and stable link to an active substance and the efficacious targeting to a target site is due to the specific structure of maleimido-functionalized core of Formula (IV).

In another aspect the invention relates to a supramolecular aggregate for use in targeting, and optionally delivering, an active substance A to the target site. Preferably the active substance is a drug.

The resulting supramolecular aggregates can be used, for example, in the field of vaccines, as ligands for GPCR (agonists as well as antagonists), as antibiotics, as diagnostics (eventually, for PWT2 in complex with a radionuclide) and in all the fields where the welding of a single molecule onto a multifunctional scaffold may be valuable.

In the invention PWT2 resulted not only to provide for a specific link to a thiol group of an active substance, but also to provide for the complexation of a broad and large number of structures. Specifically, for PWT2, the structure resulted capable to complex metals as radioisotopes.

The supramolecular aggregates of the invention do not affect the biological activity of the active substance A. Specifically the inventors showed that, in case of N/OFQ, the formation of the supramolecular aggregates does not affect the pharmacological activity (full agonism) of N/OFQ. In addition they showed that in vivo duration of action of the PWT2-N/OFQ derivative is dramatically increased compared to that of N/OFQ. For exemplificative purposes general procedure to prepare PWT2, their reaction with a thiol-containing or derived substance A are below reported.

Synthesis of the Maleimido Cores (General Procedure for the Synthesis of PWT2)

In FIG. 1 the general procedure for preparing the maleimido core coined as PWT2 is reported. The commercially available compounds 6 and 7 were reacted in the presence of the activating mixture WSC/Oxp to give in one step the desired product PWT2 in high yield.

PWT2 was then purified by preparative HPLC as explained below and their exact mass spectra is reported in FIG. 2.

General Procedure for Preparative HPLC Purification of PWT2

Crude compound PWT2 as obtained as above was purified by preparative reversed-phase HPLC using a Water Delta Prep 4000 system with a Jupiter column C18 (250×30 mm, 300 A, 15 μm spherical particle size). The column was perfused at a flow rate of 20 mL/min with mobile phases A ($H_2O$ in 0.1% TFA) and B (60% $CH_3CN$ in 0.1% TFA) and the following gradient: t0 A90%; t25 A40%; t30 A20%; t35 A 90% was employed for the elution of compounds.

The maleimido functionalized core (PWT2) is then reacted with active substance containing or derived with a thiol group. The exemplificative general procedure to link the thiol-containing active substance A and the maleimido functionalized core (PWT2) follows.

General Procedure of Thio-Michael Addition Reaction Between PWT2 Core and Molecules Containing a Thiol Group To a stirred solution of PWT2 (mmol 0.00169) in $CH_3CN/H_2O$ (1 mL) a solution of thiol containing active substance A (mmol 0.00744, 10% excess) in $CH_3CN/H_2O$ (1 mL) was added followed by $NaHCO_3$ 5% (0.1 mL). The reaction was stirred at room temperature and monitored by analytical HPLC. PWT2 core react completely and disappear from HPLC chromatogram in few minutes. Then the reaction mixture is purified directly by preparative HPLC to give the final product in high yield.

The examples relating to the detailed procedure for preparing PWT2 and their reaction with thiol-containing substance A follow.

Example 1. Detailed Procedure for the Synthesis of PWT2 (Reference to FIG. 1)

PWT2. To a stirred solution of compound 6 (1.1 mmol) in (DMF) (5 mL) at 0° C., WSC (1.2 mmol) and Oxp (1.2 mmol) were added. After 10 min a solution of compound 7 (0.25 mmol) in DMF (3 mL) was added and the reaction mixture stirred for 4 h. After evaporation of the solvent, the residue was purified by preparative HPLC to give a highly hygroscopic white solid after lyophilization.

Example 2. Detailed Procedure for Preparing Supramolecular Aggregate of PWT2 with Nociceptin/Orphanin FQ(N/OFQ-$NH_2$)

To a stirred solution of PWT2 (mmol 0.00169, MW 1062, mg 1.8) in $CH_3CN/H_2O$ (1 mL) a solution of [Cys18]N/OFQ-NH2×5TFA (mmol 0.00744, MW 2482, mg 18.5) in $CH_3CN/H_2O$ (1 mL) was added followed by $NaHCO_3$ 5% (0.1 mL). The reaction was monitored by analytical HPLC and appear to be completed in 5-min. The reaction mixture was purified by preparative HPLC to give the desired product (PWT2-N/OFQ) in quantitative yield.

Chemical formula and HPLC profile of PWT2-N/OFQ is reported in FIG. 3. Its mass spectrum is reported in FIG. 4.

The high chemoselectivity and strength of the thio-Michael reaction together with the use of 10% excess of A-SH respect cores allow the complete consumption of the maleimido moiety independently from the peptide length.

The different chemical-physical properties of the final supramolecular aggregate respect the A-SH monomer allow an easy chromatographic purification of the reaction mixture with the possibility to recover not only the 100% of the desired final product but also the 10% excess of A-SH employed to bust to completion the reaction.

The above prepared supramolecular aggregate was tested for biological activity.

Example 3

Biological Activity of the Supramolecular Aggregate of the Invention (PWT2 Derivate of N/OFQ)

The aim of the present experiments was to pharmacologically characterize the in vitro and in vivo actions of PWT2 derivative of the nociceptin/orphanin FQ (N/OFQ) peptide. To this aim in vitro experiments were performed using cells expressing the N/OFQ peptide (NOP) as well as classical opioid (the MOP, DOP, and KOP) human recombinant receptors and the electrically stimulated mouse vas deferens, a N/OFQ sensitive pharmacological preparation. In vivo studies were performed by measuring the actions of N/OFQ and PWT2-N/OFQ on mouse locomotor activity.

Material and Methods

Calcium mobilization—CHO cells stably co-expressing the human NOP, or KOP, or MOP receptor and the C-terminally modified $G\alpha_{qi5}$ and CHO cells expressing the DOP receptor and the $G\alpha_{gG66Di5}$ protein were generated as previously described (Camarda et al., Naunyn Schmiedebergs Arch Pharmacol. 379, (2009) 599-607; Camarda and Calo, Methods Mol Biol. 937, (2013) 293-306). Cells were maintained in culture medium consisting of Dulbecco's MEM/HAM'S F-12 (50/50) supplemented with 10% foetal calf serum, penicillin (100 IU/ml), streptomycin (100 μg/ml), fungizone (2.5 μg/ml), geneticin (G418; 200 μg/ml) and hygromycin B (200 mg/ml). Cell cultures were kept at 37° C. in 5% CO2 humidified air. In all cases experimental cultures were free from selection agents (hygromycin B, G418). When confluence was reached (3-4 days), cells were sub-cultured as required using trypsin EDTA and used for experimentation. Cells were seeded at a density of 50,000 cells/well into 96-well black, clear-bottom plates. After 24 hours incubation the cells were loaded with medium supplemented with 2.5 mM probenecid, 3 μM of the calcium sensitive fluorescent dye Fluo-4 AM and 0.01% pluronic acid, for 30 min at 37° C. Afterwards the loading solution was aspirated and 100 μl/well of assay buffer: Hank's Balanced Salt Solution (HBSS) supplemented with 20 mM HEPES, 2.5 mM probenecid and 500 μM Brilliant Black (Aldrich) was added. Stock solutions (1 mM) of N/OFQ, DPDPE, dynorphin A, dermorphin, and PWT2-N/OFQ (as prepared in above example 1) were made in distilled water and stored at −20° C. SB-612111 was solubilized (10 mM) in DMSO. Serial dilutions of the ligand for experimental use were made in HBSS/HEPES (20 mM) buffer (containing 0.03% BSA fraction V). After placing both plates (cell culture and compound plate) into the FlexStation II (Molecular Device, Union City, Calif. 94587, US), fluorescence changes were measured. On-line additions were carried out in a volume of 50 μl/well. To facilitate drug diffusion into the wells in antagonist type experiments, the present studies were performed at 37° C. and three cycles of mixing (25 μl from each well moved up and down 3 times) were performed immediately after antagonist injection to the wells.

Electrically stimulated mouse vas deferens—Tissues were taken from CD1 (30-35 g, Harlan, Italy) or CD1/C57BL6/J-129 NOP(+/+) or NOP(−/−) male mice. The mouse vas deferens were prepared as previously described (Calto et al., Eur J Pharmacol. 311, (1996) R3-5). Tissues were suspended in 5 ml organ baths containing heated Krebs solution (composition in mM: NaCl 118.5, KCl 4.7, KH2PO4 1.2, NaHCO3 25, glucose 10 and CaCl2 2.5) oxygenated with 95% O2 and 5% CO2. The bath temperature was set at 33° C. Tissues were continuously stimulated through two platinum ring electrodes with supramaximal rectangular pulses of 1 ms duration and 0.05 Hz frequency. A resting tension of 0.3 g was applied to the vas deferens. The electrically evoked contractions (twitches) were measured isotonically with a strain gauge transducer (Basile 7006, UgoBasile s.r.l., Varese, Italy) and recorded with the PC based acquisition system Power Lab (ADInstrument, USA). Following an equilibration period of 60 min, the contractions induced by electrical field stimulation were stable. At this time, cumulative concentration-response curves to N/OFQ, PWT2-N/OFQ or DPDPE were performed (0.5 log unit steps). In some experiments concentration response curves to agonists were performed in the absence or presence of SB-612111 (15 min preincubation time).

Locomotor activity—All experimental procedures adopted for in vivo studies complied with the standards of the European Communities Council directives (86/609/EEC) and national regulations (D.L. 116/92). Male CD-1 mice (30-38 g, Harlan, Italy) and CD1/C57BL6/J-129 NOP (+/+) or NOP(−/−) male mice were used. They were housed in Plexiglas® cages (Tecniplast, Italy), under standard conditions (22° C., 55% humidity, 12 h light—dark cycle, lights on 7.00 am) with food and water ad libitum for at least 5 days before experiments began. Experiments were performed according to the procedures previously described (Guerrini et al., J Med Chem. 52, (2009) 524-529). For these experiments the ANY-maze video tracking system was used (Ugo Basile, application version 4.52c Beta). Mice were positioned in a square plastic cage (40×40 cm), one mouse per cage. Four mice were monitored in parallel. Mouse horizontal activity was monitored by a camera while vertical activity was measured by an infrared beam array. Animals locomotion was recorded for 60 min. The parameters measured were cumulative distance travelled (total distance in m that the animal travelled during the test), immobility time (the animal is considered immobile when 90% of it remains in the same place for a minimum of 2.5 s), and the number of rearings (the number of beam breaks due to vertical movements). N/OFQ and PWT2-N/OFQ, were given intracerebroventricularly (i.c.v., 2 μl/mouse). Free hand i.c.v. injections were given, under light isofluorane anaesthesia (just sufficient to produce a loss of the righting reflex), in the left ventricle according to literature procedures (Laursen and Belknap, J Pharmacol Methods. 16, (1986) 355-357. Data analysis and terminology—In vitro data were expressed as mean±sem of at least three separate experiments. In calcium mobilization experiments, maximum change in fluorescence, expressed as percent over the baseline fluorescence, was used to determine agonist response. Non-linear regression analysis using GraphPad Prism software (5.0) allowed logistic iterative fitting of the resultant responses and the calculation of agonist potencies and maximal effects. Agonists potencies were given as $pEC_{50}$ (the negative logarithm to base 10 of the molar concentration of an agonist that produces 50% of the maximal possible effect). SB-612111 antagonist properties were evaluated in inhibition response curve experiments vs. a fixed concentration of N/OFQ or PWT2-N/OFQ approximately corresponding to its $EC_{50}$; the antagonist potency was expressed as $pK_B$ derived from the following equation:

$$pK_B = -\log(IC_{50}/([2+([A]/EC_{50})^n]^{1/n}-1))$$

where $IC_{50}$ is the concentration of antagonist that produces 50% inhibition of the agonist response, [A] is the concentration of agonist, $EC_{50}$ is the concentration of agonist producing a 50% maximal response and n is the Hill coefficient of the concentration response curve to the agonist.

In tissues experiments the antagonist effect of SB-612111 has been assessed by performing concentration response curve to agonists in the absence and in the presence of a fixed concentration of antagonist. SB-612111 potency was derived from the Gaddum Schild equation:

$$pK_B = -\log((CR-1)/[antagonist])$$

assuming a slope value equal to unity, where CR indicate the ratio between agonist potency in the presence and absence of antagonist.

In vivo data are expressed as mean±sem of n animals. Data were analysed using one-way analysis of variance (ANOVA) followed by Dunnett post hoc test. Differences were considered statistically significant when p<0.05.

Results

Figure 5:
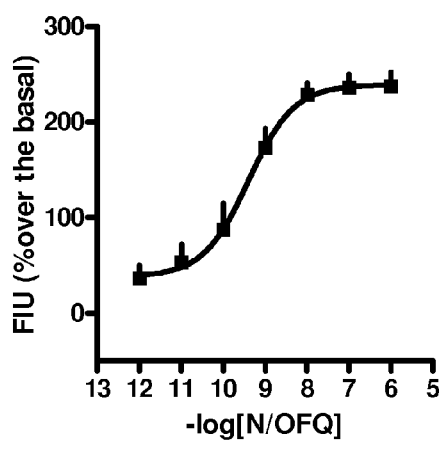
FIG. 5. Calcium mobilization assay performed on CHONOP+G$\alpha_{qi5}$ cells. Concentration response curve to N/OFQ, PWT2-N/OFQ (left panels). Inhibition response curve to SB-612111 against the stimulatory effect of N/OFQ and PWT2 derivative (right panels). Data are mean±sem of at least 4 experiments made in duplicate.
Figure 5:
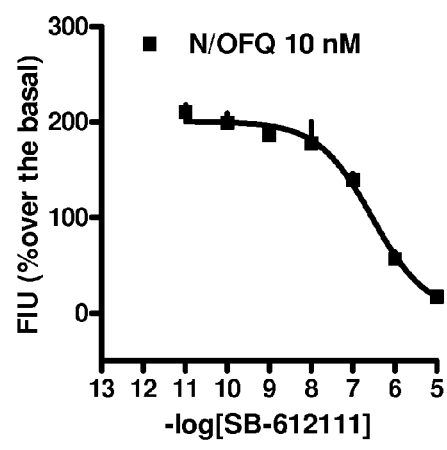
Figure 5:
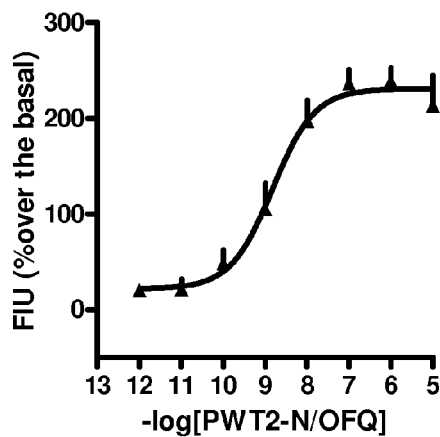
Figure 5:
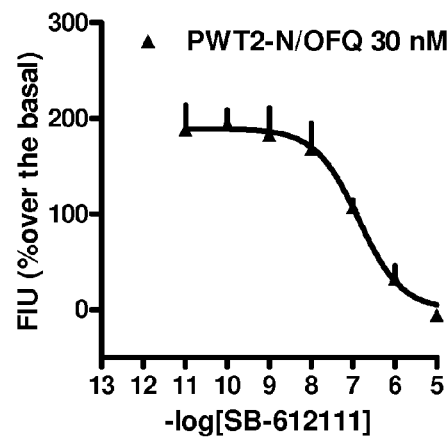

Calcium mobilization assay—In $CHO_{NOP}$ cells stably expressing the $G\alpha_{qi5}$ chimeric protein and human NOP recombinant receptor, N/OFQ and its PWT2 derivative evoked a concentration dependent stimulation of calcium release (FIG. 5, left panels). N/OFQ displayed high potency ($pEC_{50}$ 9.39) and maximal effects (237±15% over the basal values). The PWT2 derivative of N/OFQ mimicked the peptide stimulatory effects showing similar maximal effects but slightly lower potency ($pEC_{50}$ 8.83). When tested in CHO cells expressing the $G\alpha_{qi5}$ protein but not the NOP receptor, N/OFQ and its PWT derivative were found inactive up to 1 μM (data not shown). Inhibition response experiments were performed by testing increasing concentrations (10 pM-10 μM) of the standard NOP antagonist SB-612111 against a fixed concentration of agonist approximately corresponding to its $EC_{80}$ (10 nM for N/OFQ and 30 nM for PWT2-N/OFQ). SB-612111 concentration dependently inhibited the stimulatory effect of N/OFQ, displaying a $pK_B$ value of 8.01 in line with previous studies (8.16, Camarda et al., Naunyn Schmiedebergs Arch Pharmacol. 379, (2009) 599-607). Similar results were obtained challenging the antagonist against the stimulatory effect of PWT2-N/OFQ ($pK_B$ 8.23) (FIG. 5, right panels).

TABLE 1

Calcium mobilization studies. Effects of N/OFQ and its PWT derivatives in CHO cells expressing the human NOP receptor and the $G\alpha_{qi5}$ chimeric protein.

| | $E_{max}$ | $pEC_{50}$ ($CL_{95\%}$) | SB-612111 $pK_B$ |
|---|---|---|---|
| N/OFQ | 237 ± 15 | 9.39 (9.23-9.57) | 8.01 (7.84-8.18) |
| $PWT_2$-N/OFQ | 239 ± 14 | 8.83 (8.47-9.18) | 8.23 (7.87-8.59) |

In order to assess the selectivity of action of PWT2-N/OFQ, calcium mobilization experiments were also performed in cells expressing chimeric G protein and the classical opioid receptors MOP, DOP and KOP. In this series of experiments dermorphin, DPDPE and dynorphin A were used as standard agonists for MOP, DOP and KOP, respectively. In cells expressing the MOP receptor dermorphin evoked concentration dependent stimulatory effects with $pEC_{50}$ of 9.29 ($CL_{95\%}$ 9.19-9.38) and maximal effects of 135±21% (Table 2). The stimulatory effect of dermorphin were mimicked by dynorphin A that was however approx 300 fold less potent. In these cells DPDPE, N/OFQ and PWT2-N/OFQ were found inactive up to 1 μM. In cells expressing the DOP receptor DPDPE evoked concentration dependent stimulatory effects with $pEC_{50}$ of 9.57 ($CL_{95}\%$ 9.03-10.11) and maximal effects of 86±14% (Table 2). Dynorphin A was also able to elicit calcium mobilization in these cells being however 100 fold less potent. All the other agonists were inactive up to 1 μM. Finally, in KOP cells dynorphin A stimulated calcium release in a concentration dependent manner with $pEC_{50}$ of 10.04 ($CL_{95\%}$ 9.93-10.16) and maximal effects of 225±10%. All other agonists were inactive in these cells. Collectively the results obtained in these experiments with standard ligands are in line with findings from literature (Reisine, Neuropharmacology 34, (1995) 463-472). Results obtained with PWT2-N/OFQ demonstrated that the application of these chemical modifications do not affect the selectivity over classical opioid receptors displayed by the natural peptide N/OFQ.

TABLE 2

Calcium mobilization studies. Potencies of N/OFQ, its PWT derivatives, and standard opioid agonists in CHO cells expressing the human NOP or classical opioid receptors and chimeric proteins.

| | NOP | MOP | DOP | KOP |
|---|---|---|---|---|
| N/OFQ | 9.39 | inactive | inactive | inactive |
| $PWT_2$-N/OFQ | 8.83 | inactive | inactive | inactive |
| Dermorphin | inactive | 9.29 | inactive | inactive |
| DPDPE | inactive | inactive | 9.57 | inactive |
| Dynorphin A | inactive | 6.67 | 7.73 | 10.04 |

Inactive: inactive up to 1 μM.

Figure 6:
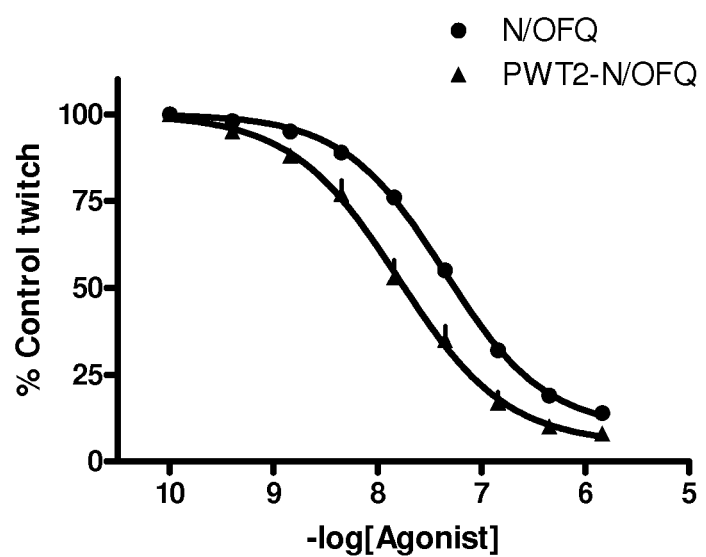
FIG. 6. Concentration response curve to N/OFQ and PWT2-N/OFQ in the electrically stimulated mouse vas deferens. The values are means±sem of 3 separate experiments.
Figure 7:
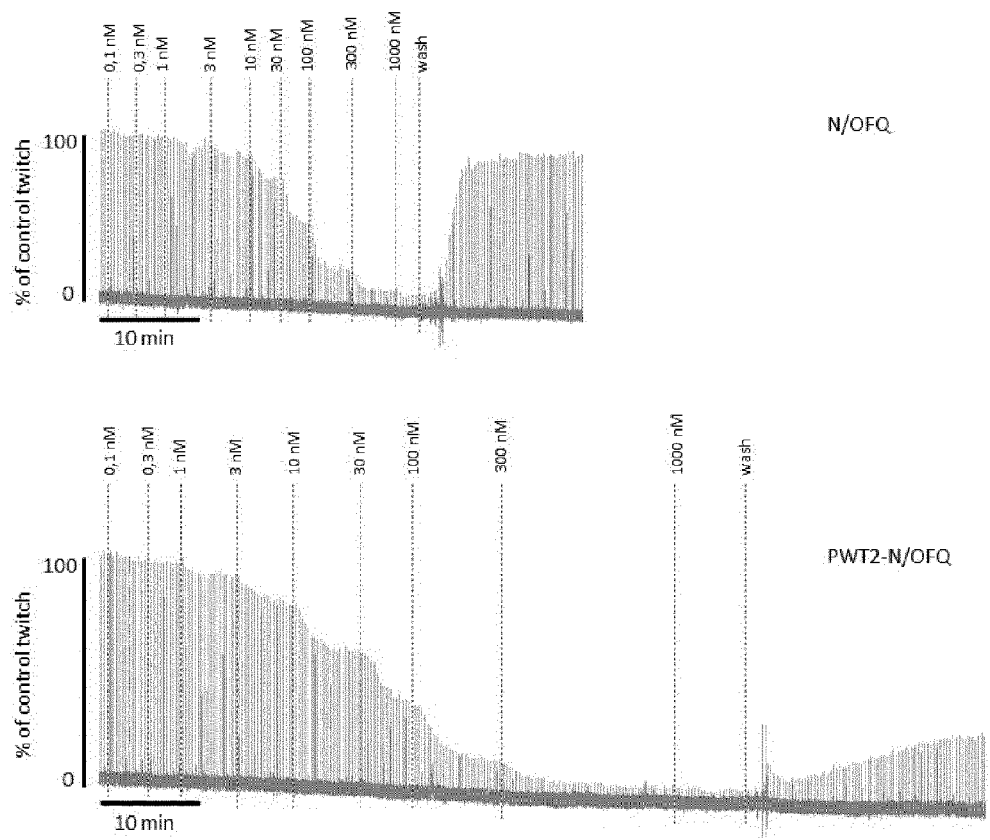
FIG. 7. Typical tracing of a concentration response curve to N/OFQ (top) and PWT2-N/OFQ (bottom). Note the slow kinetic of PWT2-N/OFQ action and lack of reversal after washing.

Electrically stimulated isolated tissue experiments—In the isolated mouse vas deferens N/OFQ inhibited the twitch response to electrical field stimulation in a concentration dependent manner ($pEC_{50}$ 7.37 ($CL_{95\%}$ 7.29-7.45), $E_{max}$=88±1% inhibition of control twitch) (FIG. 6). PWT2-N/OFQ mimicked the inhibitory effect of N/OFQ producing similar maximal effects but showing approximately 3 fold higher potency. (FIG. 6). Interestingly enough, the inhibitory effect induced by N/OFQ takes place immediately after adding the peptide to the bath and was immediately reversible after washing the tissue (FIG. 7). On the contrary, PWT2-N/OFQ induced a slow inhibitory effect which reaches the plateau only after 10 min. More importantly the effects induce by PWT2-N/OFQ were rather resistant to washing (FIG. 7).

Figure 8:
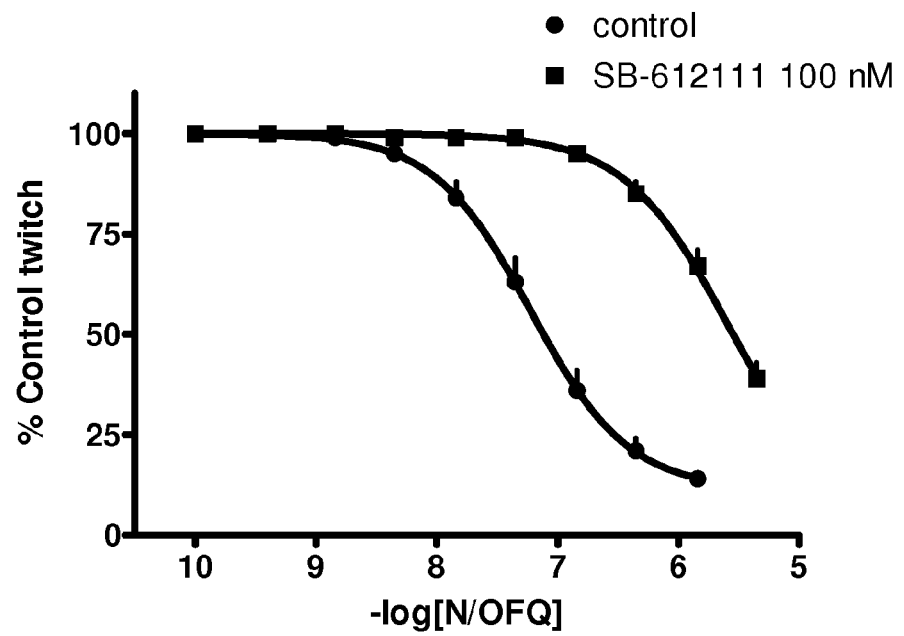
FIG. 8. Concentration-response curve to N/OFQ (top panel), PWT2-N/OFQ (bottom panel) obtained in the absence (control) and in the presence of SB-612111 (100 nM) in the electrically stimulated mouse vas deferens. The values are means±sem of at least 3 separate experiments.
Figure 8:
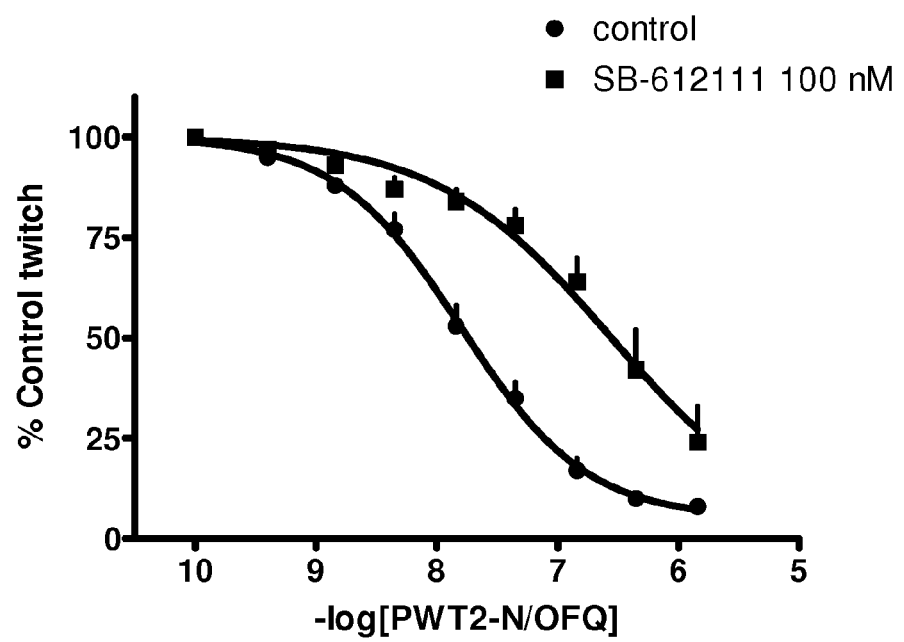

As shown in FIG. 8, the effects of N/OFQ and of the PWT2-N/OFQ were evaluated in the electrically mouse vas deferent in the absence and presence of the NOP selective antagonist, SB-612111. SB-612111 100 nM did not modify per se the control twitches but produced a rightward shift of the concentration response curve to N/OFQ without modifying the maximal effect induced by the agonist (FIG. 8, top panel). A $pK_B$ value of 8.48 was derived from these data. This value of antagonist potency is superimposable to that previously reported in literature (8.50 (Spagnolo et al., J Pharmacol Exp Ther. 321, (2007) 961-967). Similar findings were obtained by challenging SB-612111 versus PWT2-N/OFQ ($pK_B$ 8.22).

TABLE 3

Effects of N/OFQ and its PWT derivatives in the electrically stimulated mouse vas deferens.

| | $E_{max}$ | $pEC_{50}$ | SB-612111 $pK_B$ ($CL_{95\%}$) |
|---|---|---|---|
| N/OFQ | 88 ± 1 | 7.37 (7.29-7.45) | 8.48 (8.19-8.77) |
| $PWT_2$-N/OFQ | 93 ± 2 | 7.78 (7.57-7.99) | 8.22 (7.61-8.83) |

Figure 9:
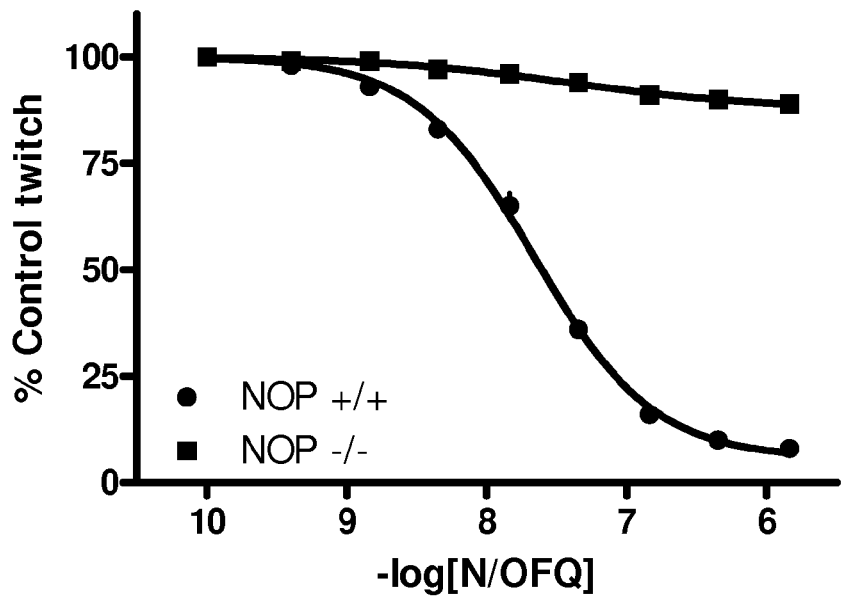
FIG. 9. Concentration-response curve to N/OFQ (top panel), PWT2-N/OFQ (bottom panel) obtained in vas deferens tissues taken from NOP(+/+) and NOP(−/−) mice. The values are means±sem of 3 separate experiments.
Figure 9:
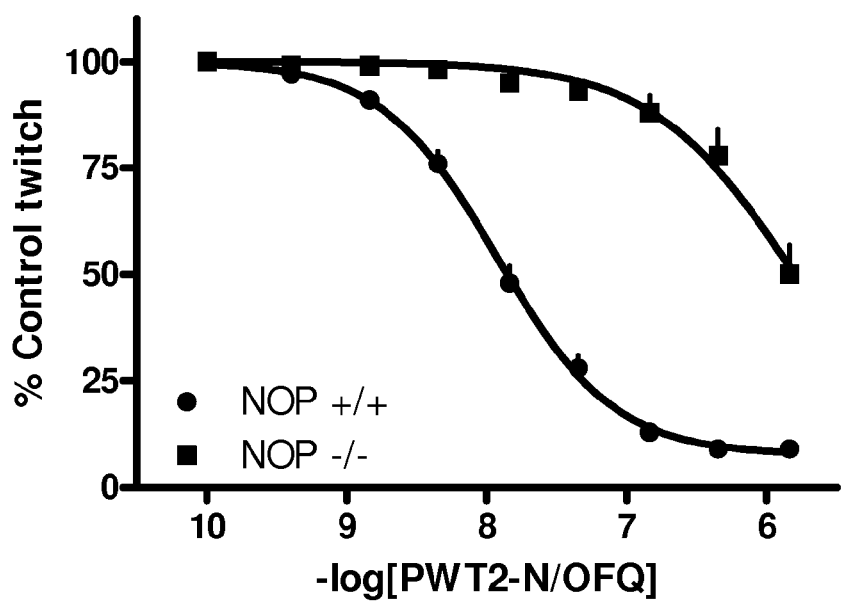

The effects of N/OFQ and PWT2-N/OFQ, and those elicited by the selective DOP receptor agonist DPDPE were investigated in the electrically stimulated mouse vas deferens taken from NOP(+/+) and NOP(−/−) mice. N/OFQ inhibited the electrically induced contractions in a concentration dependent manner with a potency value of 7.68 ($CL_{95\%}$ 7.53-7.83) and maximal effect of 92±2% in tissues taken from NOP(+/+) mice being virtually inactive up to micromolar concentrations in those taken form NOP(−/−) animals (FIG. 9 top panel). On the contrary the selective DOP receptor agonist DPDPE produced similar inhibitory effects in NOP(+/+) and NOP(−/−) tissues (Table 4). These results confirmed previous findings (Fischetti et al., Peptides. 30, (2009) 248-255). Under the same experimental conditions PWT2-N/OFQ was assayed in tissues taken from NOP(+/+) and NOP(−/−) mice. In NOP(+/+) tissues, PWT2-N/OFQ mimicked the inhibitory effect of N/OFQ showing higher potency (pEC$_{50}$ 7.92) and similar maximal effect (FIG. 9). In NOP(−/−) tissues PWT2-N/OFQ maintained the ability to inhibit the electrically induced contractions showing however more than 100 fold reduced potency (FIG. 9). The values of potency and maximal effects obtained with N/OFQ, PWT2-N/OFQDPDPE have been summarized in Table 4.

TABLE 4

Effects of N/OFQ, PWT2 supramolecular aggregate, and DPDPE in mouse vas deferens tissues taken from NOP(+/+) and NOP(−/−) animals

| | NOP(+/+) | | NOP(−/−) | |
|---|---|---|---|---|
| | pEC$_{50}$ | E$_{max}$ | pEC$_{50}$ | E$_{max}$ |
| N/OFQ | 7.68 (7.53-7.83) | 92 ± 2 | inactive | |
| PWT$_2$-N/OFQ | 7.92 (7.74-8.10) | 91 ± 2 | 5.85 (5.55-6.15) | ND |
| DPDPE | 8.45 (8.19-8.71) | 91 ± 3 | 8.42 (8.16-8.68) | 94 ± 3 |

Figure 10:
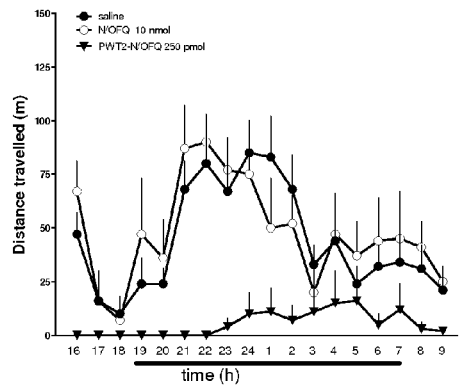
FIG. 10. Mouse locomotor activity. Effects of equieffective i.c.v. doses of N/OFQ (10 nmol), PWT2-N/OFQ (0.25 nmol) on animal distance travelled (top panels), immobility time (middle panels), and rearings (bottom panels). Results are displayed as time course from 4 PM to 9 AM (left panels) and as cumulative effects (right panels) Data are mean±sem of 10-12 mice per group. *p<0.05 vs saline according to ANOVA followed by the Bonferroni's test for multiple comparisons.
Figure 10:
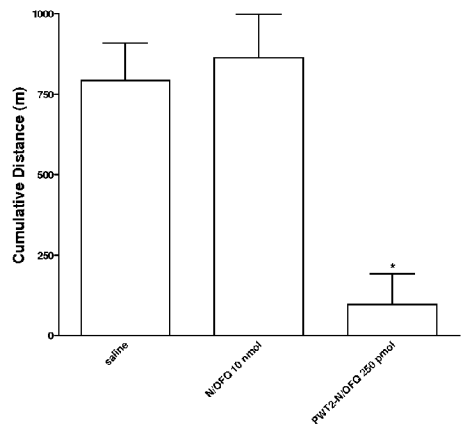
Figure 10:
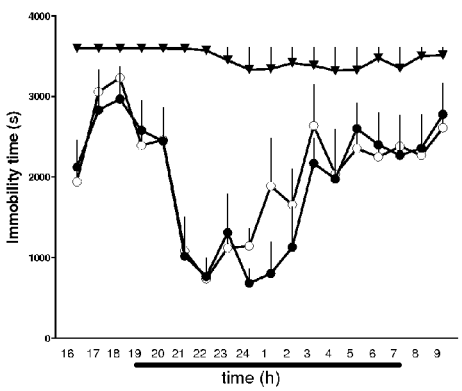
Figure 10:
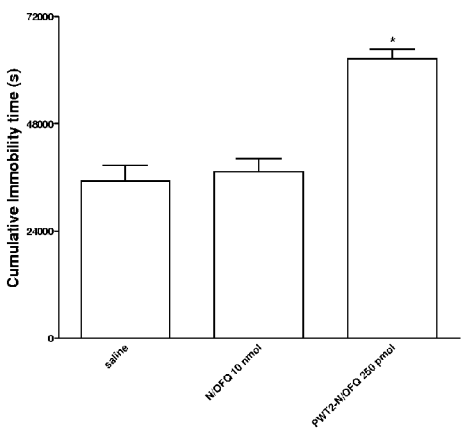
Figure 10:
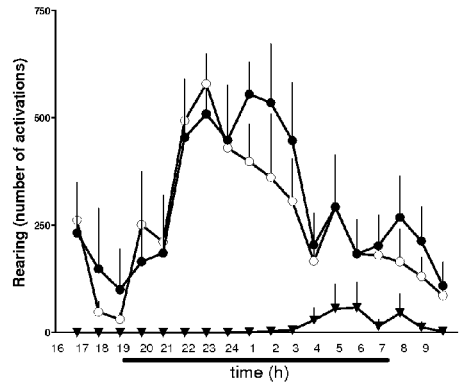
Figure 10:
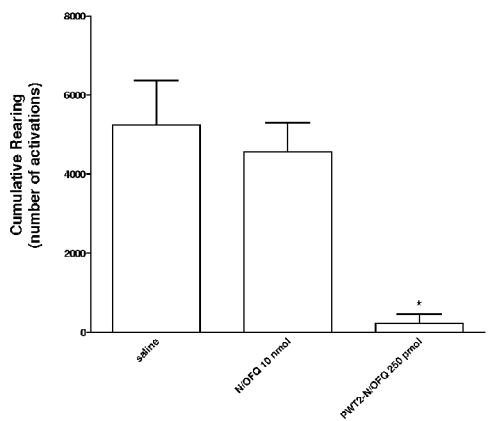

ND: maximal effect could not be determined because the concentration response curve was incomplete In vivo studies—It is known that N/OFQ given supraspinally produces biphasic effects on locomotor activity in rodents: at high doses (nmol range) the peptide elicits a robust inhibitory effect while at low doses (pmol range) it may increase locomotion (for review see Calo et al., Br J Pharmacol. 129, (2000) 1261-1283). In a series of experiments the acute effects of N/OFQ and PWT2-N/OFQ given i.c.v. on spontaneous locomotor activity were evaluated in CD-1 mice. In these experiments mouse locomotor activity was recorded for 120 min. N/OFQ produced biphasic effects: at relatively low doses (pmole range) the peptide produced short lasting stimulatory effects while at higher doses (nmole range) it produced inhibitory effects. PWT2-N/OFQ mimicked the effects of the natural peptide being however about 40 fold more potent. In addition PWT2-N/OFQ displayed slow onset of action and prolonged effects compared to the natural peptide. In order to investigate their different in vivo duration of action-N/OFQ, the effects of equieffective doses of N/OFQ (10 nmole) and PWT2-N/OFQ (at 0.25 nmole) were measured in an overnight experiment. In particular mice were injected i.c.v. at 11 AM and their locomotor activity was measured from 3 PM to 9 AM of the following day. As shown in FIG. 10 mice injected with N/OFQ displayed a locomotor behaviour similar to that of saline injected animals. On the contrary animals injected with PWT2-N/OFQ displayed statistically significant reduced distance travelled and rearing behaviour associate with increased immobility time for the whole time course of the experiment. These results demonstrated that the supramolecular aggregate displayed higher potency in vivo associated with very long lasting effects.

Finally the in vivo selectivity of action of PWT2-N/OFQ has been investigated in knockout studies. NOP(+/+) and NOP(−/−) mice were injected with saline or PWT2-N/OFQ (0.25 nmole) and their locomotor activity assessed for 120 min post injecton. As summarized in Table 5, PWT2-N/OFQ produced a statistically significant reduction of distance travelled and rearings in NOP(+/+) but not in NOP(−/−) mice.

TABLE 5

Effects of PWT2-N/OFQ on locomotor activity of NOP(+/+) and NOP(−/−) mice.

| | NOP(+/+) | | NOP(−/−) | |
|---|---|---|---|---|
| | Saline | PWT2-N/OFQ | Saline | PWT2-N/OFQ |
| Distance travelled (m) | 230 ± 26 | 104 ± 19* | 170 ± 10 | 203 ± 26 |
| Immobility time (s) | 1805 ± 378 | 3305 ± 390 | 2558 ± 454 | 2372 ± 525 |
| Rearings (n) | 911 ± 175 | 96 ± 19* | 663 ± 135 | 625 ± 181 |

*p < 0.05 vs saline, according to the Student t test for unpaired data.

Collectively in vitro and in vivo studies demonstrated that the supramolecular aggregate of N/OFQ behave as potent full agonist at human recombinant and native animal NOP receptors. The PWT2 modification has a slight effect on selectivity but this is associated in vivo with higher potency and a huge impact on duration of action which is multiplied by several folds compared to that of the native sequence.

The invention claimed is:

1. A supramolecular aggregate of formula (VI)

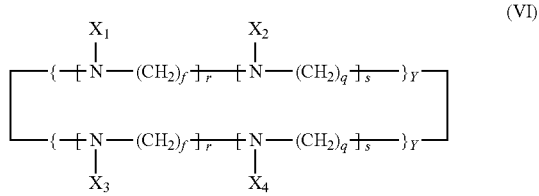

(VI)

wherein f is 3, q is 2, r and s are equal to 1, Y is 1, and $X_1$, $X_2$, $X_3$ and $X_4$, independently to each other, are a moiety of Formula (I)

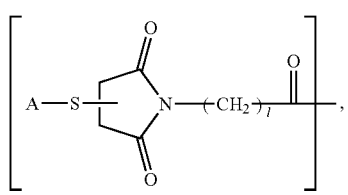

(I)

wherein in Formula (I)
A is an active substance
and I is 3.

2. The supramolecular aggregate according to claim 1, wherein A is an opioid peptide or neuropeptide S (NPS).

3. The supramolecular aggregate according to claim 2, wherein A is an opioid peptide selected from the group consisting of enkephalin, dermorphin, deltorphin, dynorphin, endomorphin, and nociceptin/orphanin FQ.

4. A maleimido functionalized core of formula PWT2

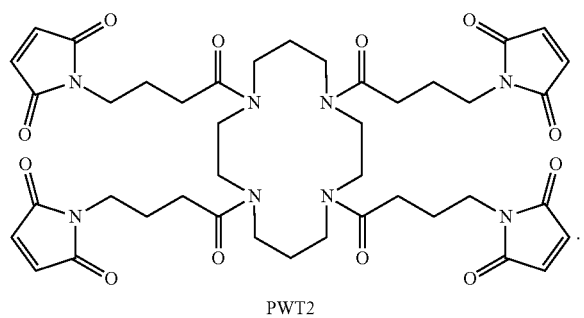

PWT2

5. A process for preparing the supramolecular aggregate according to claim 1 comprising the step of reacting in a thiol-Michael addition n(A-SH) a compound of Formula (VII)

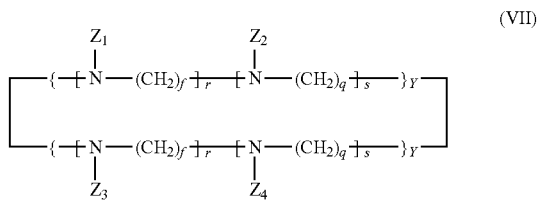

(VII)

wherein f is 3, q is 2, r and s are equal to 1, Y is 1, and $Z_1$, $Z_2$, $Z_3$ and $Z_4$, independently each other, are a moiety of Formula (II)

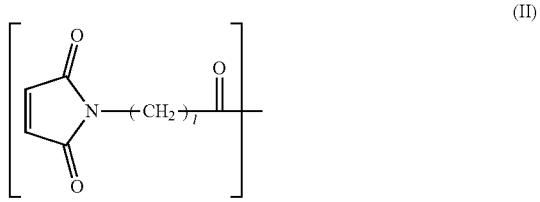

(II)

wherein I is 3.

6. A method for targeting, and optionally delivering, an active substance A to a target site comprising: administering the supramolecular aggregate of Formula (VI) according to claim 1.

7. The method of claim 6, wherein the active substance A is a drug to be targeted to a suitable receptor site.

8. The supramolecular aggregate according to claim 1, wherein A is nociceptin/orphanin FQ or NPS.

* * * * *